(12) United States Patent
Fourt et al.

(10) Patent No.: US 9,192,724 B2
(45) Date of Patent: Nov. 24, 2015

(54) REFILL MODULE FOR AN INJECTION DEVICE

(75) Inventors: Jesse Arnold Fourt, Menlo Park, CA (US); Jennifer Ellen Davis-Wilson, Mountain View, CA (US); James R. Yurchenco, Palo Alto, CA (US)

(73) Assignee: Eli Lilly and Company, Indianapolis, IN (US)

( * ) Notice: Subject to any disclaimer, the term of this patent is extended or adjusted under 35 U.S.C. 154(b) by 5 days.

(21) Appl. No.: 14/238,222

(22) PCT Filed: Aug. 21, 2012

(86) PCT No.: PCT/US2012/051702
§ 371 (c)(1),
(2), (4) Date: Feb. 11, 2014

(87) PCT Pub. No.: WO2013/032779
PCT Pub. Date: Mar. 7, 2013

(65) Prior Publication Data
US 2014/0180218 A1    Jun. 26, 2014

Related U.S. Application Data

(60) Provisional application No. 61/527,718, filed on Aug. 26, 2011.

(51) Int. Cl.
*A61M 5/315*    (2006.01)
*A61M 5/20*    (2006.01)
(Continued)

(52) U.S. Cl.
CPC ......... *A61M 5/31513* (2013.01); *A61M 5/2033* (2013.01); *A61M 5/326* (2013.01);*A61M 5/3271* (2013.01); *A61M 2005/206* (2013.01); *A61M 2005/2073* (2013.01);
(Continued)

(58) Field of Classification Search
CPC .......... A61M 5/3213; A61M 5/31511; A61M 5/3287; A61M 5/326; A61M 5/3129; A61M 5/3243; A61M 5/50; A61M 5/2033; A61M 5/2053; A61M 5/2046; A61M 5/3204; A61M 5/20; A61M 5/3271; A61M 5/2425; A61M 5/282; A61 2005/31516; A61M 2005/1787; A61M 2005/2073; A61M 2005/2474; A61M 2005/3247; A61M 2005/206; A61M 5/31515; A61M 5/35104; A61M 2005/2006
USPC .................................................. 604/218–231
See application file for complete search history.

(56) References Cited

U.S. PATENT DOCUMENTS

| 4,425,120 | A | 1/1984 | Sampson et al. |
| 4,693,708 | A | 9/1987 | Wanderer et al. |

(Continued)

FOREIGN PATENT DOCUMENTS

| DE | 102004060146 | 8/2005 |
| WO | 2009022132 | 2/2009 |
| WO | 2012073042 | 6/2012 |

*Primary Examiner* — Emily Schmidt
*Assistant Examiner* — Hamza Darb
(74) *Attorney, Agent, or Firm* — Edward J. Prein

(57) ABSTRACT

A refill module for use with a plunger assembly and having a housing (30), a syringe subassembly (70), a carrier (120) and at least one latching element (170). The syringe subassembly is shiftable within the housing from a retracted position to an injecting position at which its injection tip projects beyond the housing end. The carrier has a passageway in which a plunger of a plunger assembly is insertable for advancement of a piston (80) of the syringe subassembly. The syringe subassembly is engagable by the carrier to be moved from its injecting position to a point at which the injection tip is retracted within the housing when the carrier shifts from a first axial position to a second axial position. The at least one latching element is shiftable relative to the carrier from a retracted arrangement to a latching arrangement such that a latch surface of the latching element restricts a size of the passageway to prevent plunger withdrawal. The carrier is liftable within the housing to retract the injection tip into the housing when the at least one plunger is retracted and a latch abutment surface of that plunger engages the latch surface. When the carrier reaches the second axial position, the at least one latching element is shiftable to move the latch surface clear of the latch abutment surface to allow withdrawal of the at least one plunger from the passageway without further lifting of the carrier.

7 Claims, 14 Drawing Sheets

(51) Int. Cl.
*A61M 5/32* (2006.01)
*A61M 5/24* (2006.01)

(52) U.S. Cl.
CPC ............. *A61M 2005/2474* (2013.01); *A61M 2005/3247* (2013.01)

(56) References Cited

U.S. PATENT DOCUMENTS

| | | |
|---|---|---|
| 4,735,311 A | 4/1988 | Lowe et al. |
| 4,850,996 A | 7/1989 | Cree |
| 5,391,151 A | 2/1995 | Wilmot |
| 5,695,474 A | 12/1997 | Daugherty |
| 6,193,694 B1 | 2/2001 | Bell et al. |
| 6,387,074 B1 | 5/2002 | Horppu et al. |
| 7,320,682 B2 | 1/2008 | Cocker et al. |
| 2005/0020988 A1 | 1/2005 | Woehr et al. |
| 2005/0203466 A1 | 9/2005 | Hommann et al. |
| 2007/0129674 A1 | 6/2007 | Liversidge |
| 2008/0208140 A1* | 8/2008 | Barrelle ............ 604/198 |
| 2012/0220954 A1* | 8/2012 | Cowe ............... 604/228 |

* cited by examiner

REFILL MODULE FOR AN INJECTION DEVICE

BACKGROUND OF THE INVENTION

The present invention pertains to pharmaceutical injection devices, and, in particular, to a refill module containing medication that is used with a reusable plunger assembly.

Patients suffering from a number of different diseases frequently must inject themselves with pharmaceuticals. A variety of devices have been proposed to facilitate these injections. One type of device is an automatic injection device or autoinjector. This type of device, when triggered by a user, typically automatically inserts into the user a needle of a syringe that prior to triggering was disposed within the device housing, and then automatically injects a dose of medication through that inserted needle.

While automatic injection devices of this type may make the injection process more pleasant for some, such a device is more complex than a standard syringe. This complexity makes single use or disposable automatic injection devices more costly to manufacture than standard syringes. Automatic injection systems are known which may lessen this cost issue by utilizing a reusable plunger assembly with a disposable medication syringe. The disposable syringe serves as a replaceable refill module for the system, thereby allowing the plunger assembly to be removed from a spent syringe after the injection of the syringe's medication contents, and then reusably attached to a new, medication-filled replacement syringe for a subsequent injection with the system. While such systems are useful, users still may have various issues, depending on the system, dealing with the syringes and their associated needles. Such issues may relate to needle exposure, as well as to the task of handling, such as loading, unloading or disposing, of the syringes.

Thus, it would be desirable to provide a refill module that can overcome one or more shortcomings of the prior art.

BRIEF SUMMARY OF THE INVENTION

In one form thereof, the present invention provides a refill module mountable to a reusable plunger assembly having at least one plunger. The refill module includes a housing, a syringe subassembly, a carrier and at least one latching element. The housing has an interior hollow and first and second axial ends. The syringe subassembly includes a barrel with a medication-filled reservoir, a piston, and a needle with an injection tip. The piston is advanceable within the barrel by movement of the at least one plunger in an advancing direction to force medication from the reservoir through the needle and out the injection tip. The syringe subassembly is shiftable within the housing interior hollow from a retracted position to an injecting position by movement of the at least one plunger. The injection tip projects from the housing interior hollow and beyond the housing second axial end when the syringe subassembly is disposed in the injecting position. The carrier has a passageway in which the at least one plunger is insertable for advancement of the piston. The carrier is shiftable within the interior hollow of the housing from a first axial position to a second axial position. The syringe subassembly is engaged by the carrier to be moved axially when the carrier shifts from the first axial position to the second axial position. The syringe subassembly is disposed in the injecting position when the carrier is in the first axial position. The needle injection tip is disposed in the housing interior hollow between the first and second axial ends when the carrier is in the second axial position. The at least one latching element is shiftably mounted on the carrier and includes a cammable surface and a latch surface. The at least one latching element is shiftable relative to the carrier from a retracted arrangement to a latching arrangement by the at least one plunger engaging the cammable surface during advancement of the at least one plunger. The latch surface, when the at least one latching element is disposed in the latching arrangement, restricts a size of the passageway to prevent withdrawal of the at least one plunger from the passageway due to interference by the latch surface with the latch abutment surface. The carrier, upon retraction of the at least one plunger in a direction opposite the advancing direction while the at least one latching element is in the latching arrangement such that the latch abutment surface engages the latch surface, is lifted within the housing to shift from the first axial position to the second axial position to retract the injection tip into the housing interior hollow. At the second axial position of the carrier the at least one latching element is shiftable from the latching arrangement toward the retracted arrangement to move the latch surface clear of the latch abutment surface to allow withdrawal of the at least one plunger from the passageway without further lifting of the carrier.

One advantage of the present invention is that a refill module may be provided that allows a user to reload a drive assembly of, for example, an autoinjector with a dose of medicine in a simple and convenient fashion.

Another advantage of the present invention is that a refill module may be provided that includes an injection needle that is extended from and then retracted into the module housing during use, thereby limiting inadvertent needle stick risk as well as allowing for a better hiding of the needle from sight.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
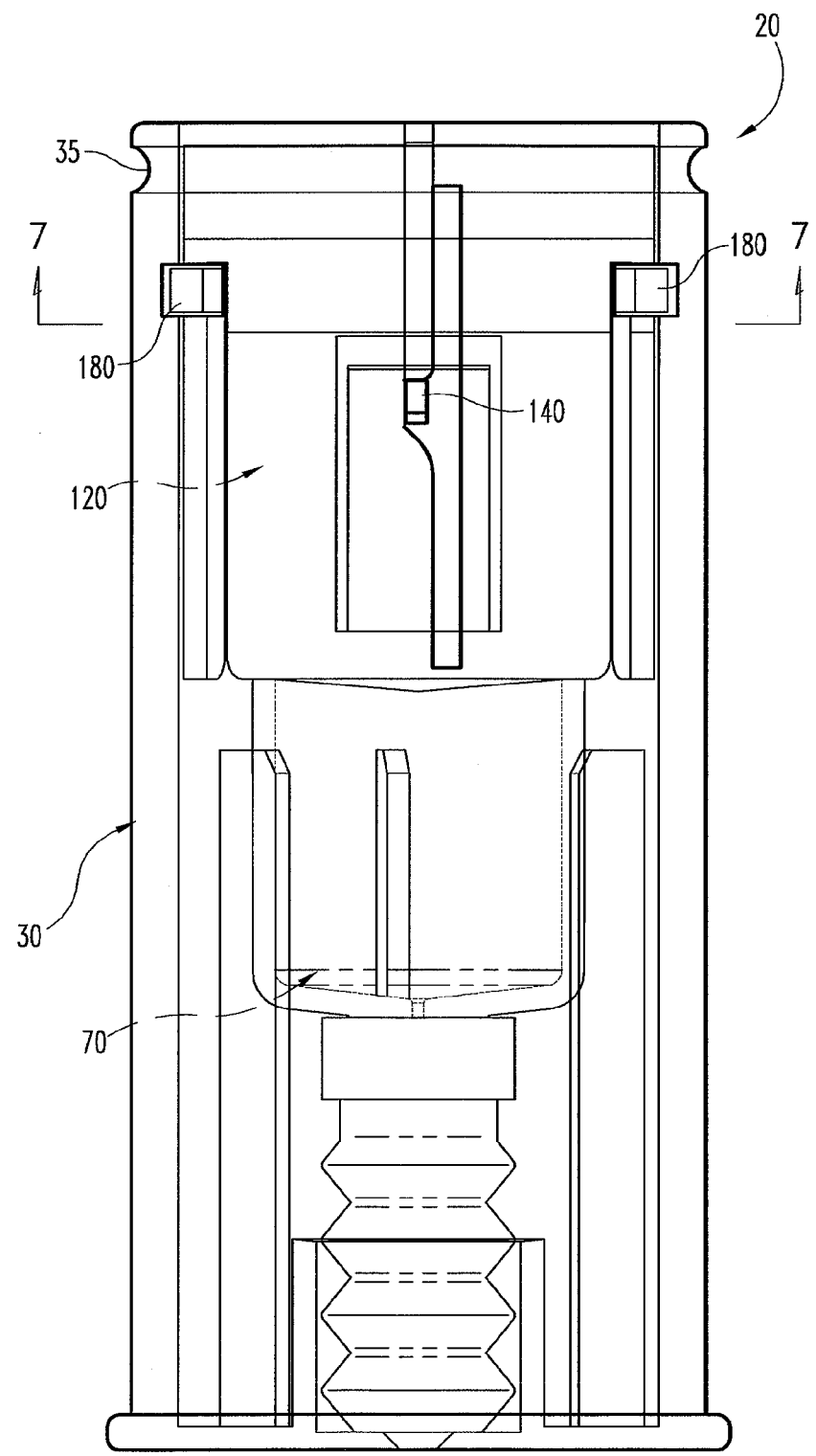
FIG. 1 is a front view of a refill module of the present invention shown separate from any portion of a suitable reusable plunger assembly with which the refill module finds beneficial application, and wherein the refill module is arranged in its stored or pre-use state.
Figure 2:
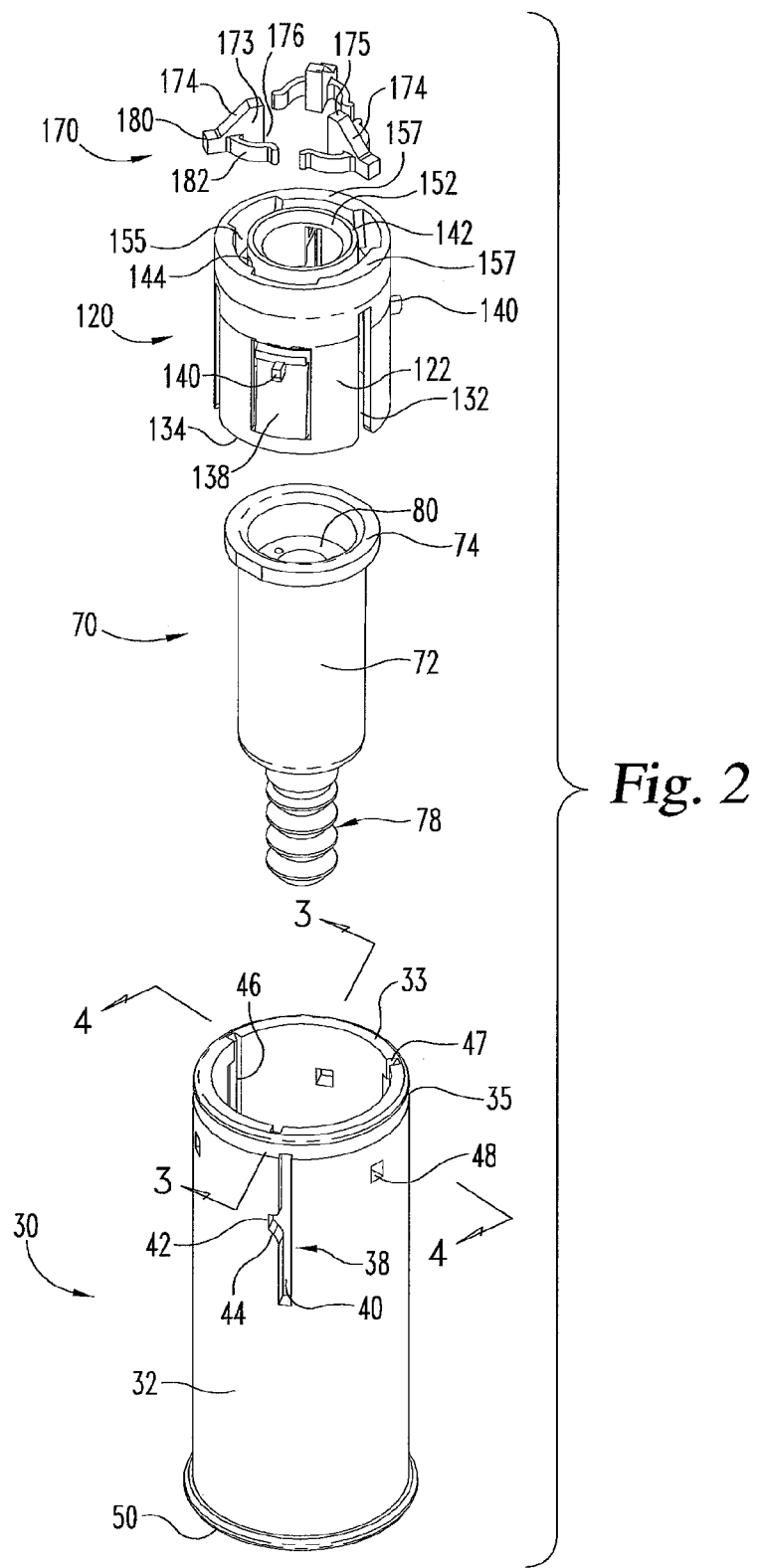
FIG. 2 is a partially exploded, top perspective view of the refill module of FIG. 1.
Figure 3:
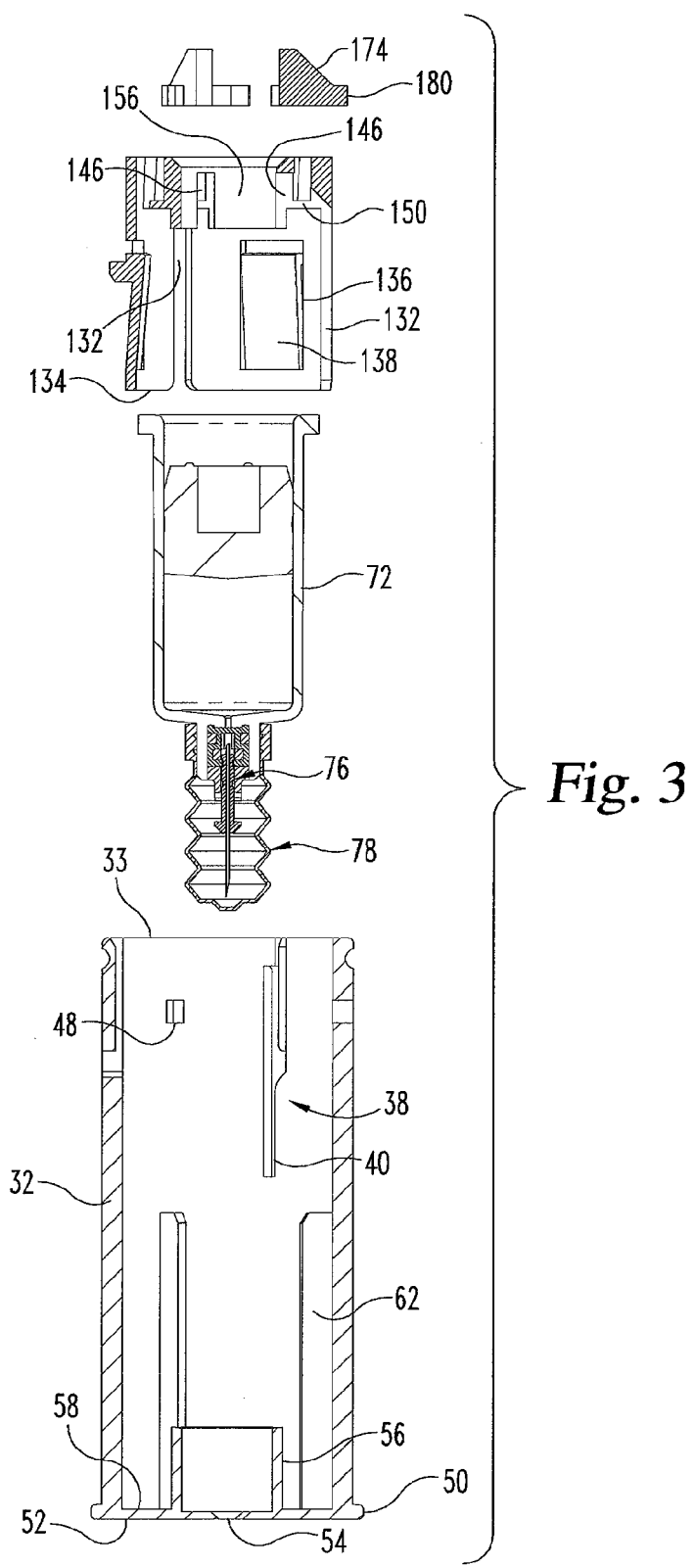
FIG. 3 is a longitudinal cross-sectional view, conceptually taken along line 3-3 of FIG. 2, of the partially exploded refill module of FIG. 2.
Figure 4:
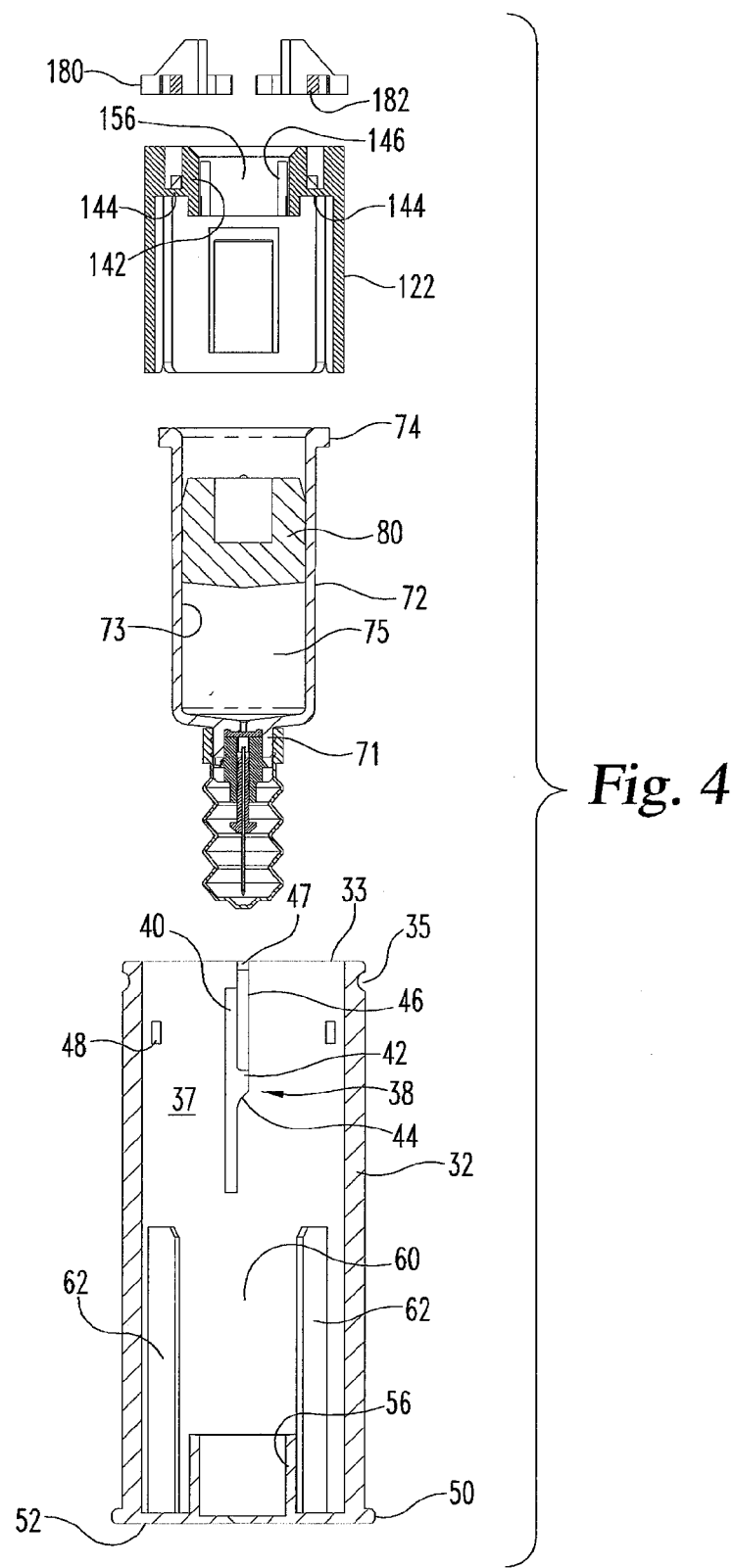
FIG. 4 is a longitudinal cross-sectional view, conceptually taken along line 4-4 of FIG. 2, of the partially exploded refill module of FIG. 2.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Referring now to FIG. 1, there is shown a first embodiment of a refill module of the present invention. The refill module, generally designated 20, is shown in its pre-use state. Refill module 20 is shown before any direct attachment or operative association with a reusable plunger assembly that interfaces with the module 20 to allow the medication contents of the module to be injected into a user through an injection needle of the module. Refill module 20 is described herein as preferably providing a single, pre-filled fixed dose of medicine, but such is illustrative as the module contents could be delivered over several doses, depending on the reusable plunger assembly and so long as an exposed needle is not problematic between doses.

With additional reference to FIGS. 2-6, refill module 20 is assembled from a housing, generally designated 30, a syringe subassembly, generally designated 70, a carrier, generally designated 120, and a set of three latching elements, generally designated 170.

Housing 30 is injection molded in a single piece, such as from a transparent plastic such as polycarbonate, with a substantially cylindrical external shape. Other shapes naturally may be employed. Housing 30 includes a tubular body portion 32 that is open at its top end 33. A circumferential groove 35 formed around the external periphery of the body portion adjacent top end 33 is adapted to allow for mounting to the reusable plunger assembly via not shown complementary fastener components of the plunger assembly. Fastening means other than groove 35 used to connect the housing directly to the reusable plunger assembly, including portions of a threading or a bayonet type fitting, or a radial rib, may be employed on body portion 32 to allow direction connection of housing 30 to the reusable plunger assembly. Still further, the fastening means may be eliminated from the housing, such as in an alternate embodiment in which the entire refill module could be mounted to the plunger assembly by being axially inserted into a complementary retainer of the reusable plunger assembly, which retainer is related to the type of retainer often used to hold cartridges in reusable injection pens, or in an alternate embodiment in which the entire refill module is inserted from the side or radially into a differently shaped retainer associated with the plunger assembly.

A set of three carrier guides are formed in the housing as indicated at 38. Guides 38 are provided as apertures that extend through the body portion wall thickness, and each guide 38 includes a longitudinally extending track 40 with a laterally or angularly projecting notch 42 along a middle section of the track length. The guides alternatively could be provided as appropriately shaped recesses formed in the inner periphery or wall of the tubular housing body portion 32.

Three guides are shown at equal angular spacing around the housing circumference for a robust design, but fewer guides, including as few as one, or even more guides, could be used. Each guide notch 42 is defined by a ramp surface 44 at its lower end, which ramp surface 44 is for rotating the carrier during the needle inserting process as described below. The guides may be modified, or the carrier guided by such guides may be modified, to reduce the possibility of the carrier keys slipping back from track 40 into notch 42 when the carrier is lifted past during needle retraction.

Along the inner wall of housing body portion 32, three longitudinally extending grooves 46 that are provided to guide the keys 140 during module assembly extend upward to housing top end 33 from the three guide notches 42. Each groove 46 includes a ramped upper end 47.

Three square openings 48 are provided though body portion 32 to accommodate complementary features of latching elements 170. Openings 48 are equally angularly spaced around the body portion circumference and are angularly spaced from the carrier guides 38.

At its bottom end, body portion 32 includes a circumferential rib 50 that projects radially outward. Rib 50 promotes stability on the skin when the module is used, as well as aids in orientation of the module for mounting to a reusable plunger assembly. Furthermore, rib 50 provides a grip feature that may aid a user in removing the refill module from the plunger assembly. A disc-shaped base section 52 of the housing closes off the bottom end of body portion 32 but for an opening 54 centrally disposed through base section 52. A cylindrical, tubular collar 56 of the housing projects upward from the upper face 58 of base section 52 within the hollow interior 60 of housing body portion 32. Collar 56 aids in locating or guiding the module syringe. Collar 56 is shown in spaced relationship with the inner periphery of body portion 32. Three guide ribs 62 of housing 30 are formed on the interior surface 37 of body portion 32 and extend upward from base section 52. Ribs 60 extend longitudinally and are equally angularly spaced within the housing body portion.

Syringe subassembly 70 is medication-filled and during use is moved axially within housing 30. The movement of syringe subassembly 70 results in its needle projecting beyond the housing 30 for insertion into a user, and then in its needle retracting, after the injection, to a protected position within the housing.

Figure 5:
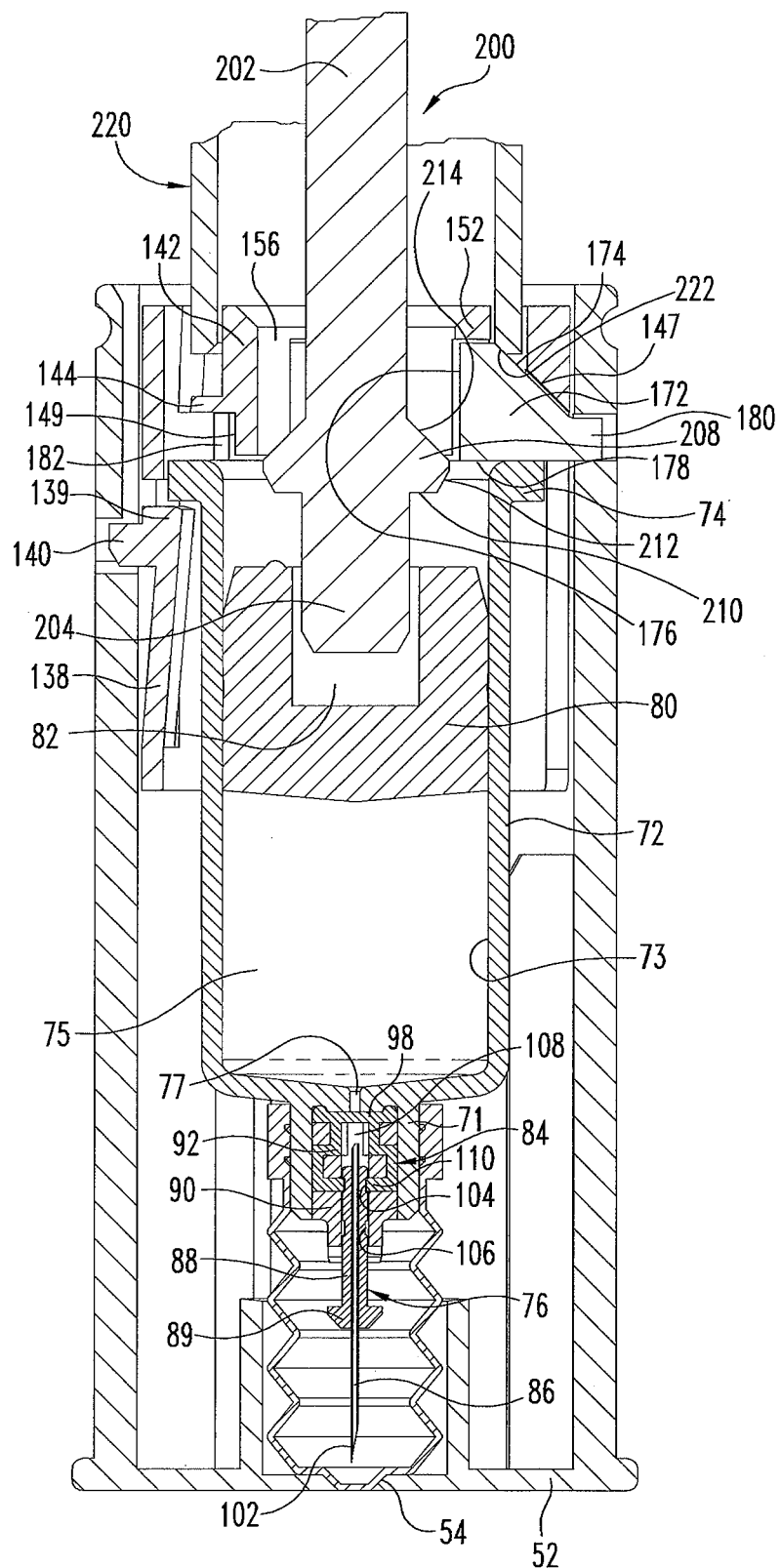
FIG. 5 is the longitudinal cross-sectional view of the refill module of FIG. 3 in an assembled or unexploded state, and wherein certain cooperating members of a suitable reusable plunger assembly are partially shown.
Figure 6:
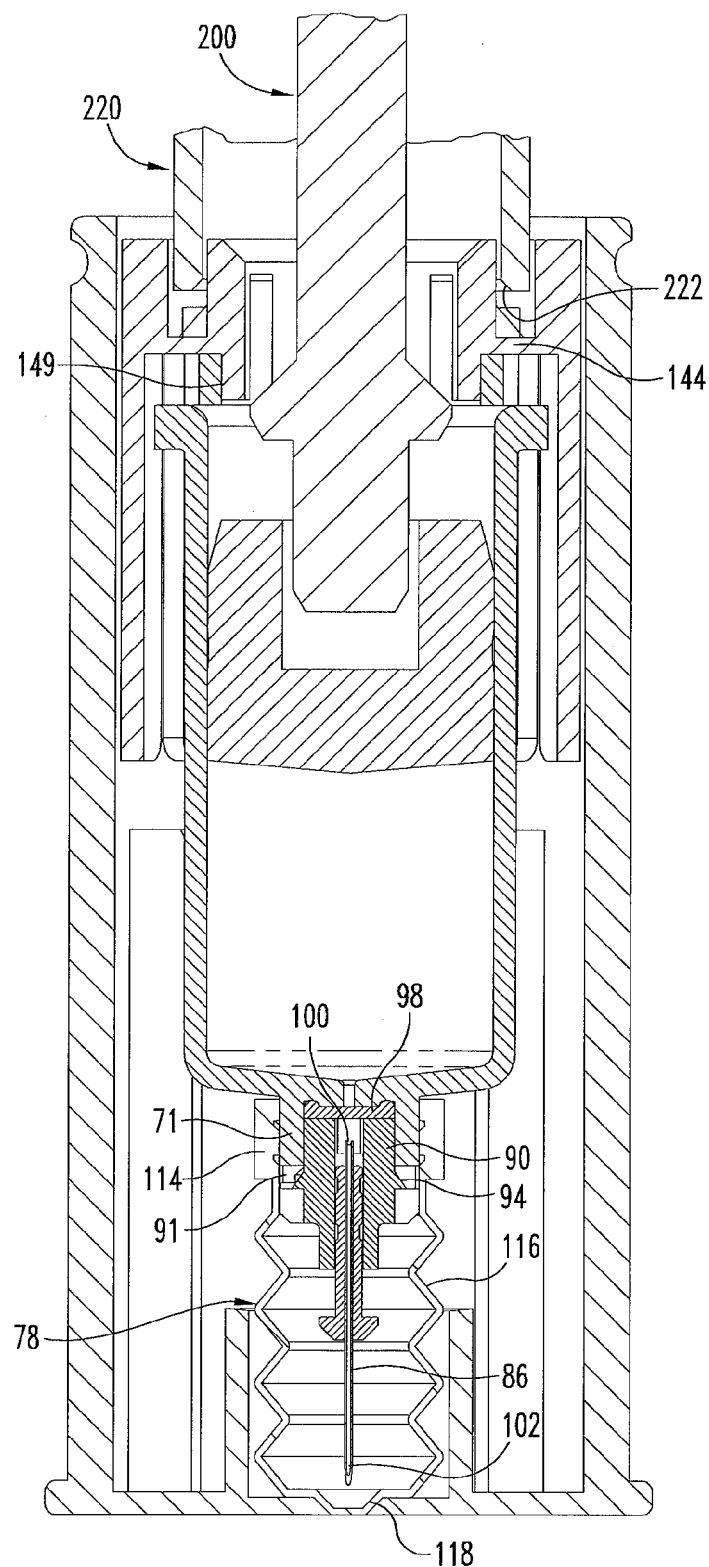
FIG. 6 is the longitudinal cross-sectional view of the refill module of FIG. 4 in an assembled state, and wherein certain cooperating members of a suitable reusable plunger assembly are partially shown.

With particular reference to FIGS. 5 and 6, syringe subassembly 70 is shown as including a barrel 72, such as made of a molded plastic material. Barrel 72 includes a cylindrical interior surface 73 that defines an interior hollow 75 that serves as a medication reservoir in which medication to be delivered is stored for use. Barrel 72 includes a radially outwardly extending, circumferential rib or flange 74 at its upper end. A stepped-down diameter neck portion of the barrel 72 forms a tubular hub or collar 71 adapted for receipt of an injection needle assembly 76 and needle cover 78 of syringe subassembly 70.

An elastomeric member or piston 80 sealingly and slidably fits with the barrel interior surface 73 to seal the top end of the medication reservoir 75. The bottom end of the medication reservoir 75 is sealed by the injection needle assembly 76.

Injection needle assembly 76 includes a hub insert 84, as well as a a double-ended cannula 86 retained in a needle carrier 88. Hub insert 84 includes a rigid, injection molded plastic base 90 with a resilient element 92 that is formed by an overmolding of base 90. Suitable materials for element 92 include a molded thermoplastic elastomer or an injection molded silicon. Hub base 90 provides for a secure attachment to the collar 71 of the syringe barrel 72 when hub insert 84 is installed within collar 71 during manufacturing assembly. One suitable attachment means is ramp-shaped protrusions 94 of base 90 as shown in FIG. 6 that fit into appropriately shaped slots 91 formed in collar 71 that together provide a bayonet fitting. A transverse slot shown at the bottom end of base 90 allows needle assembly 76 to be rotated with a tool into the collar 71 for the bayonet style attachment during manufacturing assembly. Other attachment means known in the art may be used, such as snap fits or press fits. When hub insert 84 is so installed, a septum or sealing region 98 of hub insert element 92 forms a fluid-tight seal with barrel 72 around an outlet orifice 77 of the barrel so as to form a pierceable septum that seals the bottom end of the medication reservoir 75.

Cannula 86 includes a septum piercing tip 100 at its proximal or upper end and a patient penetrating or injection tip 102 at its distal or lower end. Cannula 86 is insert molded into needle carrier 88, with its tips 100 and 102 exposed, so that the cannula and needle carrier are shiftable axially as a single unit during use as described below.

Needle carrier 88 includes first and second circumferential grooves 104 and 106 in axially spaced arrangement along the carrier length. The distal end of carrier 88 is provided with an enlarged head 89 that is sized and shaped complementary to the chamfered opening 54 in housing base section 52 so as to fit in but not pass through the opening 54.

Needle carrier 88 and cannula 86 are held within a central, axially extending hollow 108 of hub insert 84 in either of first or second axial positions. Nubs 110 of hub element 92 extend within hollow 108 and fit within either of grooves 104 or 106. During manufacturing assembly, injection needle assembly 76 is installed to the hub insert 84 such that nubs 110 fit within groove 104, in which arrangement the needle assembly 76 is retained in a first axial position relative to hub insert 84 with needle tip 100 in an axially spaced apart, non-piercing relation with septum 98. In the second axial position of the needle assembly, nubs 110 fit within groove 106, and the needle tip 100 has pierced septum 98 so as to be in flow communication with the contents of the medication reservoir 75.

Needle cover 78 maintains the sterility of cannula 86 prior to the use of refill module 20. Needle cover 78 is made in a single air-tight piece of a compression or injection molded elastomer, such as a compression molded silicone. Cover 78 is formed with a mounting ring 114, a collapsing body or bellows 116, and a tip region 118 at the lower end of cover body 116. Ring 114 fits in a sealing manner to the periphery of syringe hub 71 to maintain needle sterility. Hub 71 includes two ringing barbs on its exterior for a secure engagement with the smooth interior of ring 114. Cover body 116 fits within the interior housing collar 56 and collapses in an accordion style when axially compressed during module use. Tip region 118 is shaped to cover the chamfered housing opening 54.

Syringe subassembly 70 allows for injection without manual or user removal of any sterility cover of the injection needle, but different syringes may be employed with the refill module 20 within the scope of the invention. For example, in an alternate embodiment, a conventional staked needle syringe with a manually removable needle cover in which the injection tip is sealingly embedded may be used with suitable modification to the housing to allow for appropriate cover access. Still further, the syringe could include a needle that is in contact with the drug contents before use, but with a collapsing cover, not necessarily bellows shape, that has a distal mass in which the injection tip is sealingly embedded before use, and through which the needle tip pushes through for insertion. In still additional embodiments, a double ended cannula could push through a septum plug, distinct from an insert that retains the needle, and at the reservoir end, and a collapsible, non-bellows shaped cover. Or, and again with a dry needle before use, the syringe subassembly may employ a cork that is shifted by a blunted proximal needle tip during needle insertion.

Carrier 120 is formed as a single part in an injection molding process. One acceptable material for carrier 120 that provides suitable strength and rigidity while allowing sufficient flexibility for syringe installation is an acetal resin known as Delrin®. Carrier 120 includes a tubular body 122 that is sized to slidably fit within the hollow interior 60 in a guided manner as described below. Three slots 132 in carrier body 122 which extend longitudinally from the body bottom end 134 accommodate housing guide ribs 62 at the lower extent of carrier travel. Along a middle axial region, openings 136 formed through body 122 define three identical flexible fingers 138. The upper end of each finger 138 includes a lip 139 for syringe flange abutment. A key 140 with a ramped inward distal face projects radially outward from each finger 138 below its respective lip 139 and is sized to fit within housing guide 38 to rotationally locate the carrier 120 within housing 30. When refill module 20 is oriented in its storage or pre-use condition, keys 140 reside within guide notches 42.

Carrier 120 includes a tubular wall portion 142 that is connected to body 122 via a spanning flange 144 located along a middle region of the axial height of wall portion 142. Spanning flange 144 includes a plurality of arcuate slots for molding purposes. An annular gap 155 is formed between wall portion 142 and carrier body 122 at the carrier upper end. The upper end 152 of wall portion 142 is chamfered to promote a piston advancing plunger of the reusable plunger assembly properly inserting through the central bore or passageway 156 defined by wall portion 142. Three equally angularly spaced slots 146 formed in wall portion 142 and extending upward from the base of wall portion 142 are in angular alignment with three openings 150 in flange 144 as well as body slots 132 to accommodate the latching elements 170. Body 122 includes thicker wall sections at 157 above slots 132 to keep the gap 155 small and to provide a robust design.

Latching elements 170 are mounted on carrier 120 and are used in the retraction of the carrier and thereby the syringe subassembly after an injection. Latching elements 170 may be made from a suitably durable and resilient material such as polypropolene. Three latching elements 170 are shown at equal angular spacing and at a common height within the carrier 120. As few as one latching element 170 may be used, but the shown triangular positioning around central passageway 156 provides a secure engagement with the piston advancing plunger during its withdrawal to effect needle retraction. Still further, the three latching elements could be fabricated together as a single part.

The three latching elements 170 are identical and each includes an upstanding base 172 that includes a top edge having a flat portion 175 and an inclined or ramp-shaped surface 174 along its upper and radially outward region. Base surface 174 is complementarily shaped to an angled carrier surface 147 to fit there against when the latching element 170 is assembled to the carrier 120. Base 172 further includes an inner face 176 that is axially extending, and an underside 178 extending radially outward from the bottom end of base face 176. A square-shaped tab portion 180 projects from base 172 at a height below surface 174. Tab portions 180 are sized to fit within housing openings 48 to serve as carrier locating detents prior to use.

Each latching element 170 further includes a pair of resilient fingers or flexures 182. One flexure 182 projects from each radially-aligned side face 173 of base 172 and is angled to engage carrier surface 149. This flexure engagement with surface 149 biases latching element 170 radially outward. While this integral formation of the biasing flexure into the latching element facilitates assembly, such a biasing force, if desired, may be otherwise provided.

Refill module 20 is intended for use with a reusable plunger assembly or injection device that in most respects may be configured in any suitable manner known in the art. For example, the reusable plunger assembly may include a spring or motor or otherwise driven plunger that provides for an automatic injection, or it may be a system that is both controlled and powered completely manually. The reusable plunger assembly, for use with the refill module 20, is shown in FIGS. 5 and 6 and 8-12 as including a a pair of plungers, namely a first plunger that works with the syringe piston and is advanced for injection and then retracted for subsequent use of that device, and a second plunger for activating a system for latching the first plunger as well as advancing the syringe for needle insertion.

Piston advancing plunger 200 is a cylindrical rod 202 that is sized and shaped to be movable within the refill module 20. A distal end 204 of plunger rod 202 is sized to freely insert into a complementarily shaped cavity 82 in piston 80. Rod end 204 directly engages the elastomeric plunger at the base of the cavity 82 via abutting contact, although the advancing plunger in an alternate embodiment could drive the elastomeric piston indirectly, such as through an intervening component, such as an insert mounted to the piston that is abutted by the piston rod. As the advancing plunger 200 is not mechanically attached to the piston, the process of withdrawing the plunger from the piston after use is not complicated. The not shown proximal end of the plunger rod 202 is associated with the rest of the not shown reusable plunger assembly, and does not enter the refill module 20 during use.

Plunger 200 also includes a retraction element that cooperates with latching elements 170 to provide for needle retraction after an injection is performed. The retraction element is provided as a rib 208 that radially projects from rod 202 proximally of rod end 204. Rib 208 extends the entire circumference of rod 204 to allow for it to be latched at any angular orientation of the rod 204. The cross-section of rib 208 shown in the Figures is representative of all longitudinal cross-sections, and rib 208 includes a distal surface 210, a chamfered surface 212, and an upward facing, angled surface 214. Rib surface 210 does not abut the syringe piston in the shown embodiment, but could in alternate embodiments, such as where a differently configured piston is employed. Chamfered surface 212, which defines the largest diameter of the plunger 200 that inserts within the refill module, is sized to freely fit through the central passageway 156 defined by carrier wall portion 142, and between the inner faces 176 of latching elements 170 when the flexures 182 have biased the elements 170 radially outward. The chamfer of surface 212 aids in locating and inserting the plunger within the carrier passageway. Angled surface 214 serves as a latch abutment surface for engagement with base faces 178 of latching elements 170 that have been shifted radially inward over the biasing force of flexures 182 during use as described below. The angling of surface 214 is advantageous as if the latching elements, despite the biasing provided by flexures 182, do not shift outward sufficiently to lock the module after use, the angled surface 214 serves to cam out the latching elements to achieve such outward motion.

Latch activating plunger 220 is shown in the form of cylindrical sleeve, although differently shaped elements that are suitable to engage the latching elements may be employed. Plunger 220 includes beveled end face 222 that is used to engage latching elements 170 to drive them radially inward as plunger 220 is axially advanced within module 20. Plunger 220 in the shown embodiment also serves to drive the syringe subassembly and carrier down during needle insertion as described below. The needle insertion function need not be performed by the latch activating plunger in all embodiments, as an additional element of the injection device, or possibly the piston advancing plunger, could alternatively perform this function.

Plunger 220 is arranged coaxially with plunger rod 202, but plungers 200 and 220 can be moved axially relative to each other at least during part of the operation of the reusable plunger assembly. For example, such as with refill module 20 mounted to the reusable plunger assembly and at the start of an injection, plungers 200 and 220 are simultaneously moved axially downward to a point at which plunger rib 208 is below the latching elements 170 and the syringe subassembly has been been appropriately advanced by the plunger 220 to provide for a complete needle insertion into a user. The injection device then, without further downward movement of plunger 220, can move the plunger 200 farther downward to deliver the medication contents. After an injection, retraction of plunger 200 can occur without movement of plunger 220 until the carrier 120 is shifted upward as described below, which shifting moves plunger 220 upward as well. It will be appreciated that plunger 220 can in fact be retracted by the plunger assembly independently of the plunger 200 at any time after, for example, the plunger 200 engages the syringe piston, as the latching elements have been rotated such that tab portions 180 do not align with housing openings 48 as the tab portions would then abut the interior wall of the housing.

The above description of the plunger assembly is intended to be illustrative and not limiting, as refill modules within the scope of the present invention can be operated by differently configured and different numbers of plungers. For example, the functions performed by the plunger assembly described above, namely the activation of the latching elements, the needle insertion, the delivery of medication and the needle retraction, can be performed with two plungers that divide the functionality differently than as divided between the two plungers described above. More plungers with dedicated functionality alternatively could be used. Or, as few as a single plunger could be used with some refill modules. For example, with a refill module provided within additional openings in the carrier above the syringe barrel, a plunger assembly having only a single appropriately configured plunger could be used. That single plunger could include not only a distal end and a latch abutment surface similarly functioning to that described above, but also fingers that jut outward and downward from a middle section of that single plunger. The bottom tips of the fingers of the single plunger would abut and cam inward the latching elements of the refill module in performing the needle insertion and latching element activation function. When the refill module carrier rotates during needle insertion, the additional openings provided in the carrier would move into registry with the fingers, allowing the finger bottom tips to pass through the carrier openings and into the syringe barrel interior volume as the single plunger is advanced to force the medication contents from the module. While this modified refill module may need to be angularly aligned with the plunger assembly for use, the design of the plunger assembly with which it works is simplified from one having multiple moving plungers.

Figure 7:
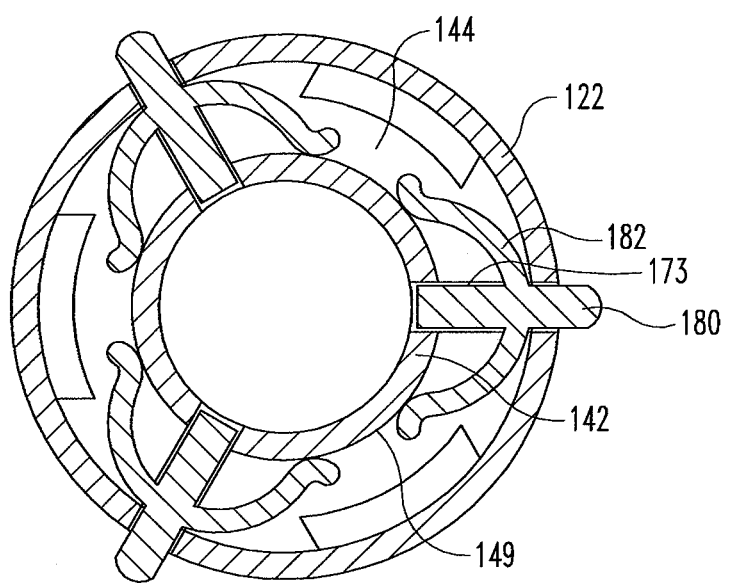
FIG. 7 is a cross-sectional bottom view, taken along line 7-7 of FIG. 1, of the assembled carrier and latching elements shown separate from of the rest of the refill module.

The refill module 20 may be assembled by the manufacturer in the following manner. The carrier 120 is first provided independent of the other components of the module 20. Each latching element 170 is then separately inserted into the bottom end of the tubular body 122 such that its tab portion 180 inserts and slides upward within carrier slot 132. Each latching element 170 is so slid upward, with its base surface 174 passing through flange opening 150, and its inner face 176 entering wall portion slot 146, until its base surface 174 abuts carrier surface 147. During this sliding upward of the latching elements, flexures 182 are manipulated to fit onto and slide along the surface 149 of wall portion 142. At this point in the assembly, the latching elements and carrier are arranged as shown in FIG. 7.

After all three latching elements 170 are so installed, the complete syringe subassembly 70 is installed by inserting it into the tubular body 122 from below and with the barrel rib 74 end leading. Syringe subassembly 70 can be freely inserted until the barrel rib 74 encounters the flexible fingers 138. When sufficient force is applied to the syringe subassembly, the flexible fingers 138 are forced outward until the barrel rib 74 passes thereby, at which point the flexible fingers 138 snap back inward with lip 139 fitting beneath the underside of barrel rib 74 to prevent the syringe subassembly from being withdrawn downward. At such a point, further upward motion of syringe subassembly 70 is limited by abutting engagement of the underside of carrier flange 144 by the barrel rib 74 via the flexures 182 sandwiched therebetween. The syringe subassembly 70 is thus axially retained or captured within the carrier 120.

The assembled carrier 120, syringe subassembly 70, and latching elements 170 can then be installed as a unit to the housing 30, first by inserting the bottom tip of the syringe subassembly into the top of the housing and then moving it downward until carrier keys 140 are aligned with grooves 46. As downward motion into the housing is continued, flexible fingers 138 bend inward to allow keys 140 to slide within grooves 46, and during such time tab portions 180 are forced inward by a tool against the returning force provided by the bending of flexures 182 so as to be insertable within the interior of housing 30 and to slide along the housing interior surface 37. This downward motion continues until tab portions 180 snap outward, due to the flexure provided force, into housing openings 48, thereby halting the assembly process. Keys 140 will snap outward into the opening provided by notch 42 of the carrier guide 38 just before or simultaneously with the snap outward travel of tab portions 180. At this point, the refill module 20 is configured in its ready to use arrangement shown in FIG. 1.

Refill module 20 and its benefits will be understood still further in view of the following description of its operation. Refill module 20 as shown in FIG. 1 is first mounted to a reusable plunger assembly. Although not shown in the Figures, a label may be provided on the outside of the housing, which label could extend from the bottom of groove 35 to the end of carrier 134. Such a label would obscure the carrier mechanism and indicating strip 190 from view, as well as make it more difficult for a user to poke the ends of tab portions 180 inward, while allowing the full dose of the syringe to be visible. For the shown housing configuration including groove 35, the mounting involves arranging module 20 so that plungers 200 and 220 can insert though the top end of the housing with rod distal end 204 and rib 208 smoothly entering into the central volume or passageway 156 of the carrier 120 and syringe subassembly 70, and with plunger end face 222 entering gap 155, after which point the not shown fasteners acting with groove 35 can be engaged by a user. The fact that module 20 need not be radially or angularly oriented relative to the plungers 200 and 220 facilitates the module installation. At this point, the refill module 20 and the plungers 200 and 220 are arranged as shown in FIGS. 5 and 6. It will be recognized that the plunger 200 need not be inserted into the passageway 156 during the module mounting process, but rather could be so inserted by an operation of the plunger assembly after mounting of the module is complete.

Figure 8:
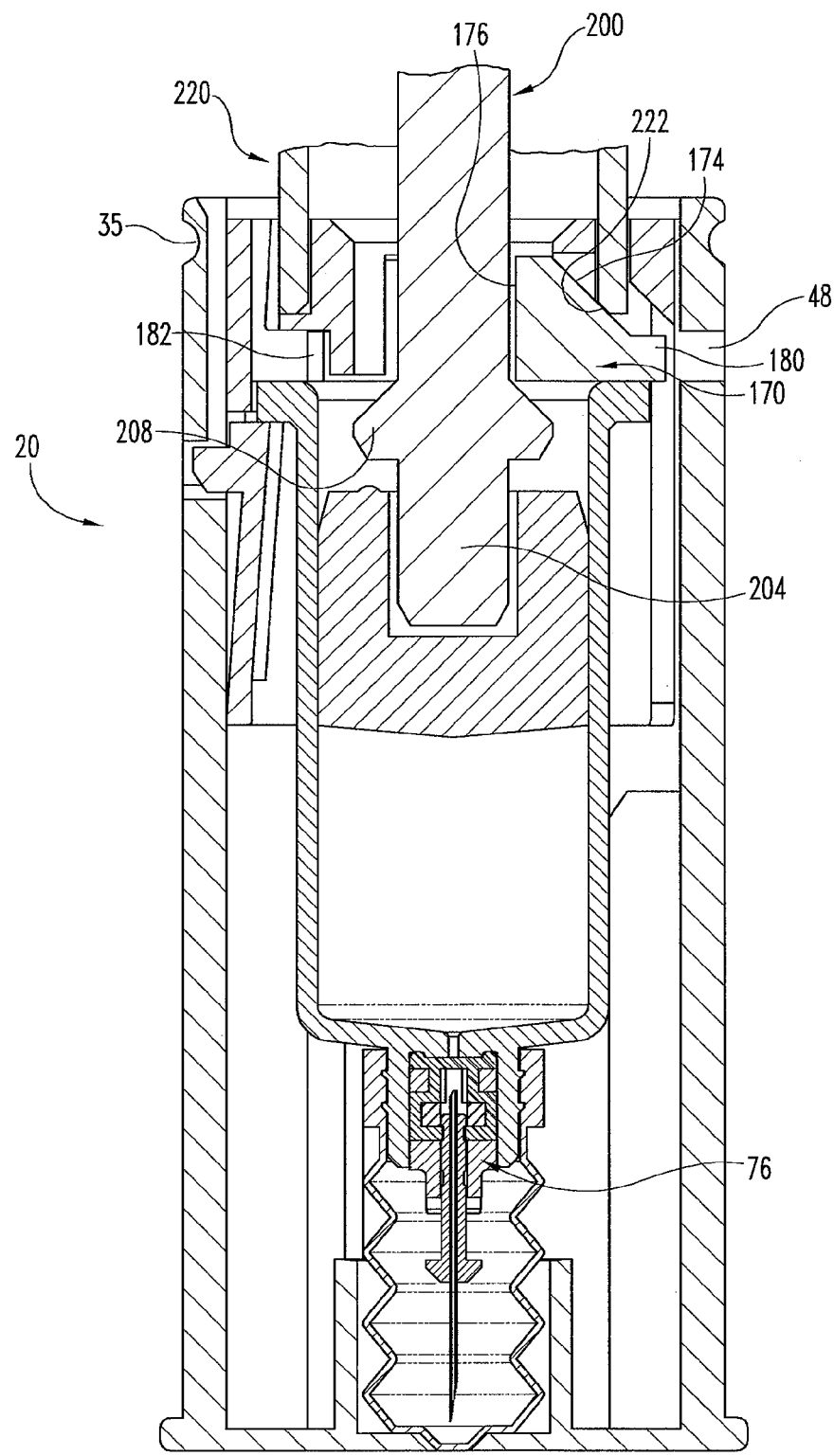
FIG. 8. is a longitudinal cross-sectional views of the refill module of FIG. 5 at a subsequent stage of its operation.

When the dose held in module 20 is intended to be delivered, the device is manipulated such that the housing base section 52 is placed against the patient's skin with the opening 54 over the intended injection site, and the reusable plunger assembly is operated, initially causing plungers 200 and 220 to be simultaneously advanced downward within housing 30. During this advancement, plunger sleeve end 222 first abuts the ramped surfaces 174 of latching elements 170, and then slides along such ramped surfaces 174 as it cams the latching elements 170 radially inward against the force of flexures 182. Latching elements 170 are moved radially inward such that the inner faces 176 are moved from their first arrangement that allowed free axial passage of plunger rib 208 to a second arrangement having a central circular opening that is smaller than the diameter spanned by rib 208, which rib 208 is below the latching elements 170 when the elements are so cammed inward, but which central circular opening still allows free passage of the rod diameter. In this second arrangement, tabs 180 no longer project radially outward into housing openings 48. Although this shifting of the latching elements is described as occurring during the dose delivery, such could alternatively occur during the refill module mounting. Furthermore, the plunger 220 could be so advanced independently of plunger 200 if plunger 200 had, for example, been sufficiently inserted into the refill module during refill module mounting. At this point, the refill module 20 and the plungers 200 and 220 are arranged as shown in FIG. 8.

As plungers 200 and 220 continue to be simultaneously advanced downward within housing 30, needle insertion into the patient occurs because the syringe subassembly 70 is driven downward by plunger 220 acting on latching elements 170 acting on syringe barrel rib 74. Plunger 200 does not yet contact syringe piston 80. Carrier 120 is also driven downward, due to barrel rib 74 acting on lip 139, and carrier 120 initially rotates slightly as well, such as about seven degrees, during this downward movement due to the twisting imparted by the guides 38 as carrier keys 140 ride along ramp surfaces 44 and into tracks 40. In FIGS. 9-12, the carrier and the other components besides the housing have all been rotated from their rotational positions in FIG. 8, but are shown similar to FIG. 8 because instead the housing in FIGS. 9-12 has been rotated the seven degrees from its position shown in FIG. 8. When so rotated, carrier slots 132 are moved into angular alignment with housing guide ribs 62 such that carrier 120 is rotatably fixed when moved further downward along the length of the ribs 62 as such ribs fit in slots 132. During the initial rotation of the carrier 120, latching elements 170 carried by the carrier are also similarly rotated to be out of angular alignment with housing openings 48, and thus do not reextend into such openings 48 during the needle retraction process, but rather abut against the housing wall surface 37, and thus the plunger 220 no longer needs to apply downward force on the latching elements once plunger 200 suitably contacts piston 80.

Figure 9:
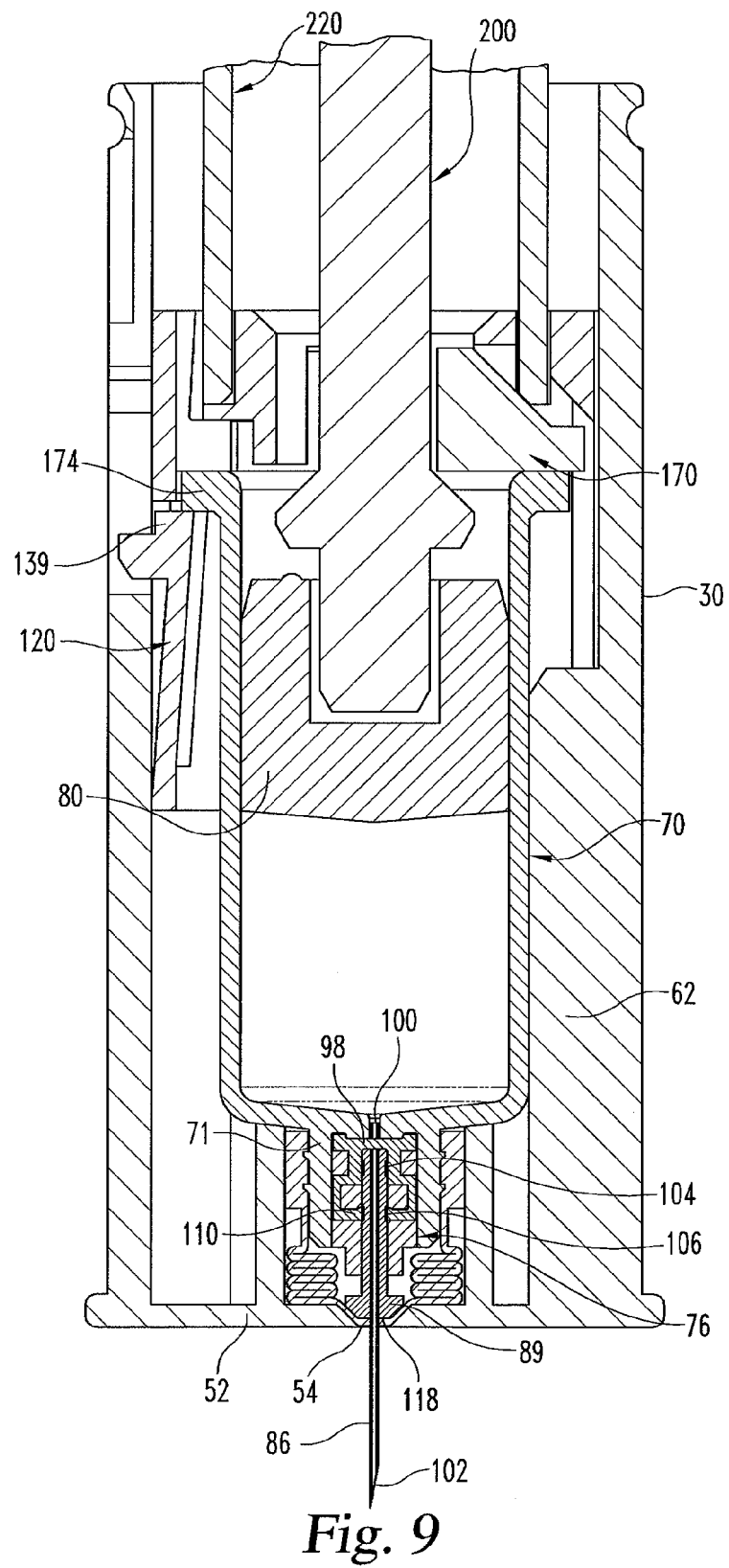
FIGS. 9-12 are longitudinal cross-sectional views of the refill module similar to FIG. 8, but through a plane rotated from the cut plane of FIG. 8 in an amount equal to the rotation of the module components relative to the housing during use, at subsequent stages of module operation.

During this simultaneous advancement downward of plungers 200 and 220 for needle insertion, needle assembly 76 initially is not in flow communication with the syringe reservoir as the needle assembly is in its first axial position in which nubs 110 fit in groove 104. As the syringe subassembly 70 moves downward, cannula tip 102 pierces cover tip region 118 and passes through housing opening 54 and into the user. The detent feature of nub 110 and groove 104 prevent the cannula 86 from moving axially relative to the syringe hub 71. As downward motion of syringe is continued to be driven by the advancement of plunger 220, needle carrier head 89 abuts housing base section 52, with the cover tip region 118 sandwiched therebetween, and still further advancement of plunger 220 overcomes the detenting of nub 110 and groove 104 such that needle assembly 76 is shifted to its second axial position where nubs 110 fit in groove 106 and with needle tip 100 piercing septum 98 to allow the syringe contents to be forced through cannula 86 and out injection tip 102. At this point, at which the barrel 72 contacts collar 56 to be physically stopped from further advancement, the refill module 20 and the plungers 200 and 220 are arranged as shown in FIG. 9, and the advancement of plunger 220 is halted.

Figure 10:
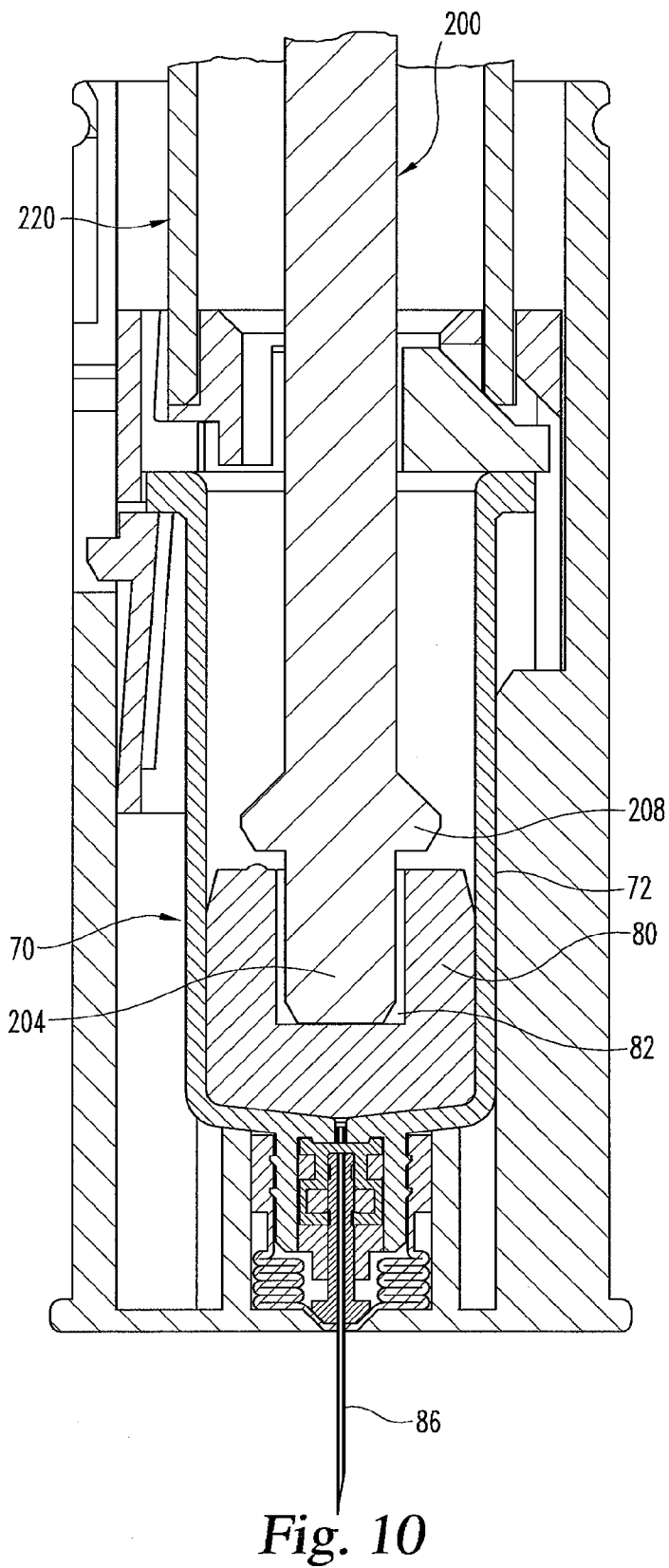

Further downward advancement of plunger 200 by the reusable plunger assembly results in the rod distal end 204 abutting piston 80 at the base of cavity 82 and driving the piston 80 downward within the barrel 72 to decrease the volume of the reservoir 75 and drive the syringe contents into the user through the needle cannula 86. When the contents of the syringe subassembly 70 have been suitably injected, the refill module 20 and the plungers 200 and 220 are arranged as shown in FIG. 10.

Figure 11:
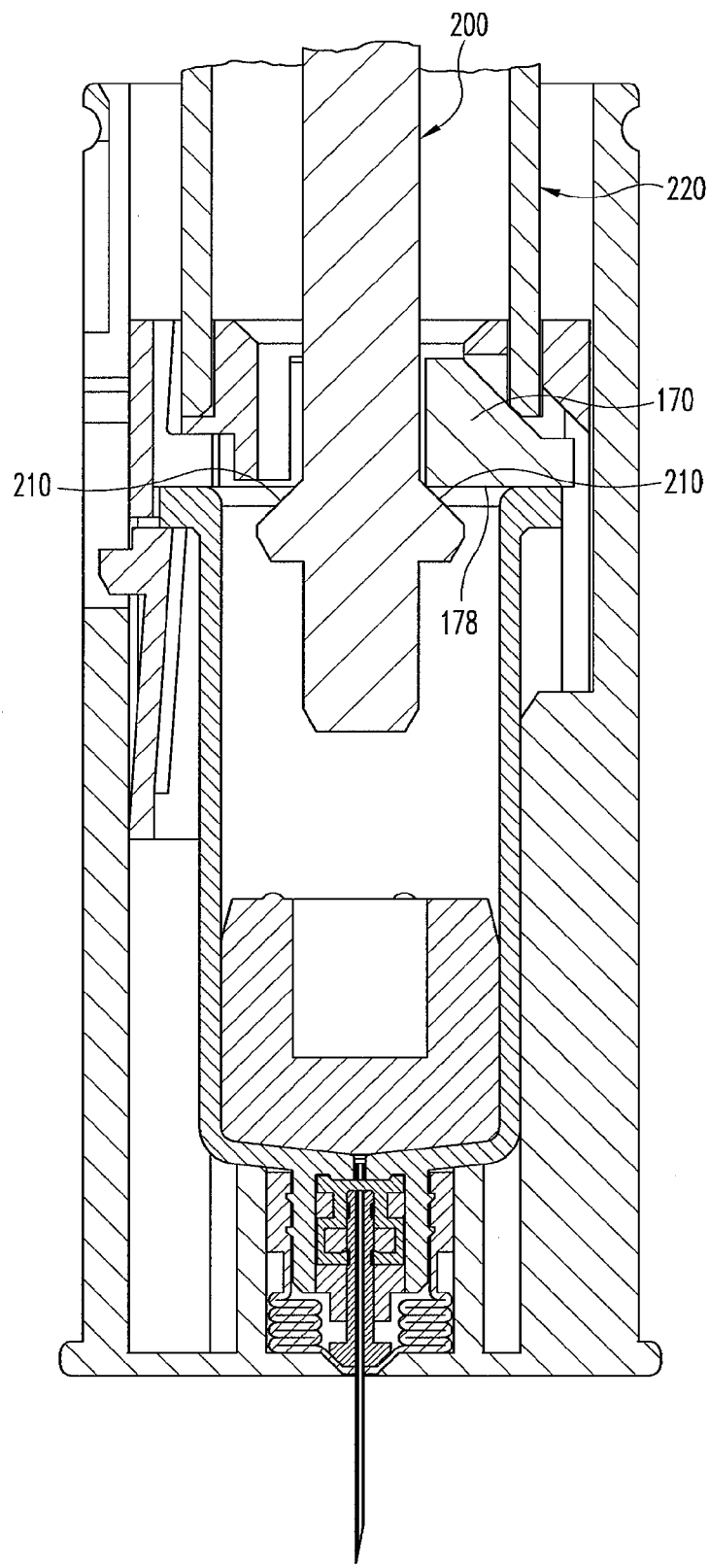

Needle retraction is performed by the reusable plunger assembly retracting the plunger 200 upward within the refill module without axial movement of plunger 220. At the start of such plunger retraction, no effect on the refill module 20 occurs as the plunger retraction progresses until latch surface 210 abuts and is thereby latched by the undersides 178 of latching elements 170 that are still in their radially inward arrangement. At this point, the refill module 20 and the plungers 200 and 220 are arranged as shown in FIG. 11. It will be appreciated that even if plunger 220 were initially retracted with the plunger 200, latching elements 170 still could be maintained in their radially inward arrangement that provides an interference for the plunger rib 208 due to the outward faces of tabs 180 abutting the interior surface of housing 30.

Figure 12:
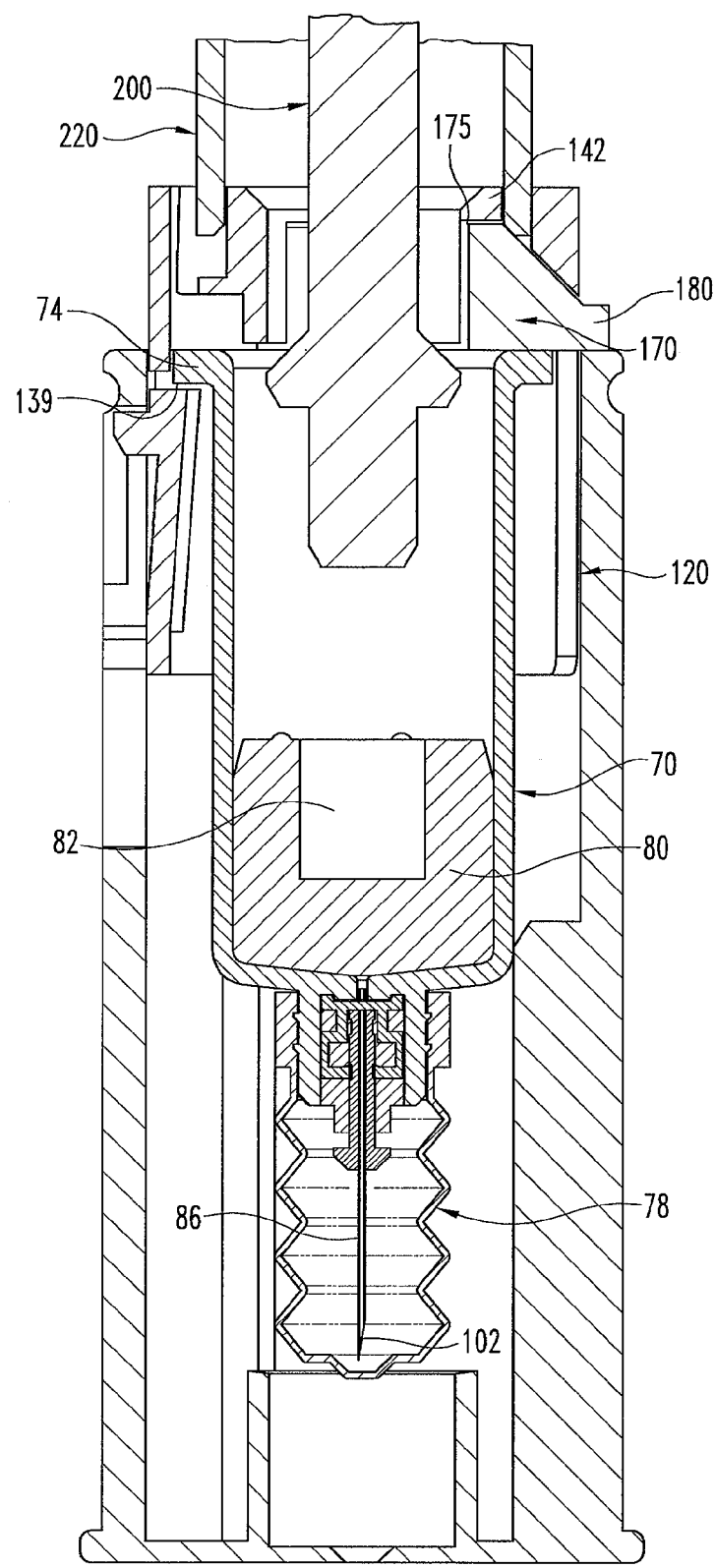

As retraction of plunger 200 is then continued, along with the self or even plunger 200 driven retraction of plunger 220, due to the relationship between top of the flexures 182 of the latching elements 170 acting on the carrier flange 144, and the carrier lips 139 acting on the syringe barrel flange 74, plunger 200 will lift the latching elements 170, carrier 120 and syringe subassembly 70 upward within the housing 30. This lifting continues until the carrier 120 is pulled partially out of the housing 30 and the latching elements 170 snap outward, due to the returning force provided by flexures 182, to their radial position occupied pre-use, at which radial position the tabs 180 radially protrude out over the top of the housing 30. In this radial arrangement of the latching elements, plunger 200 is released from its latched engagement with the latching elements 170 to allow the further withdrawal of the plunger from the refill module. At this point, the refill module 20 and the plungers 200 and 220 are arranged as shown in FIG. 12. The needle tip 102 has been fully retracted within the housing interior. Although the cover 78 is shown in FIG. 12 returned to its extended arrangement, even if, due to friction with the cannula 86, it remains in its collapsed state not covering tip 102, the likelihood of an inadvertent needle stick is reduced by virtue of the needle retraction within the housing.

Figure 13:
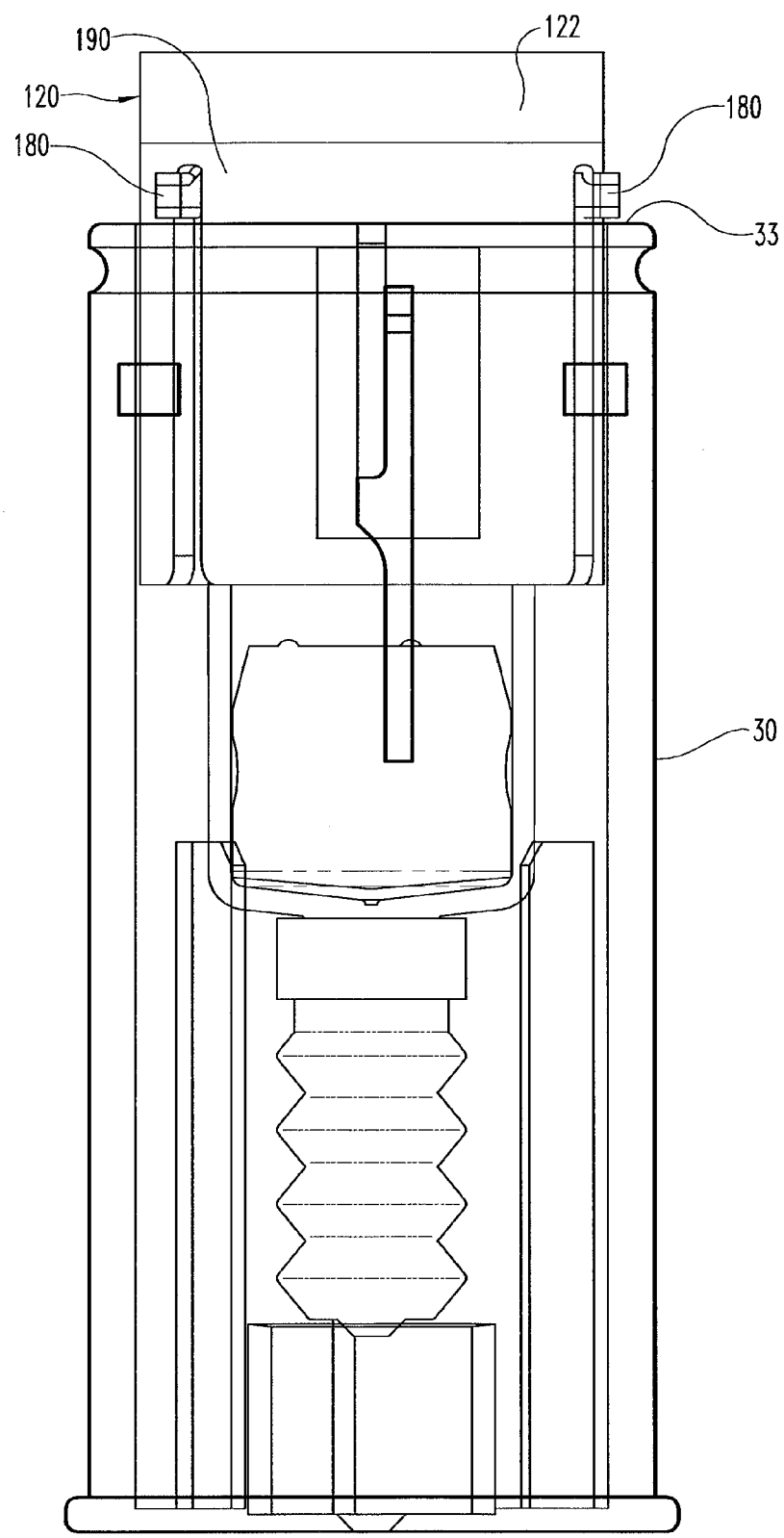
FIG. 13 is a front view of the refill module of FIG. 12 after its removal from the reusable plunger assembly.
Figure 14:
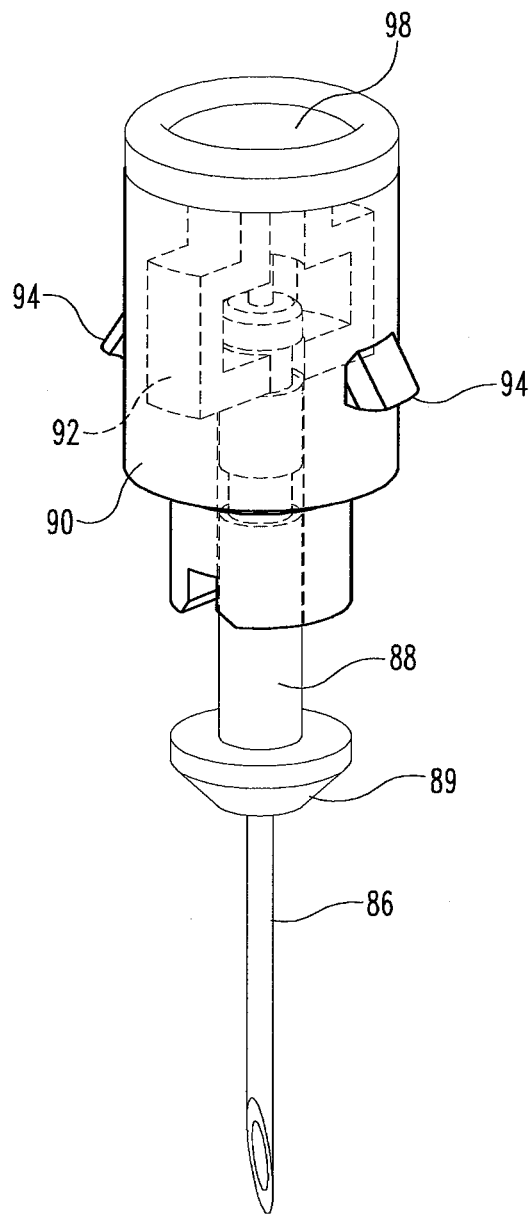
FIG. 14 is a perspective view of the injection needle assembly shown separate from the rest of the refill module.

When the reusable plunger assembly and refill module 20 are subsequently separated or detached, the refill module 20 will be as shown in FIG. 13. The used status of the refill module is apparent from the difference in its appearance from its unused state shown in FIG. 1. For example, the carrier 120 now projects above the top of housing 30 and an indicating strip 190 that extends around the radial periphery of the carrier 120 is now visible to a user. Module reuse is thwarted by tabs 180 engaging housing 30 to prevent syringe plunging The user can than discard the refill module 20 in an appropriate fashion and load the reusable plunger assembly with a new replacement module 20 for subsequent use.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

We claim:

1. A refill module mountable to a reusable plunger assembly having at least one plunger, the at least one plunger includes a latch abutment surface, the refill module comprising:
    a housing having an interior hollow and a first axial end and a second axial end;
    a syringe subassembly including a barrel with a medication-filled reservoir, a piston, and a needle with an injection tip, said piston advanceable within said barrel by movement of the at least one plunger in an advancing direction to force medication from said reservoir through said needle and out said injection tip, said syringe subassembly shiftable within the housing interior hollow from a retracted position to an injecting position by movement of the at least one plunger, said injection tip projecting from the housing interior hollow and beyond said housing second axial end when said syringe subassembly is disposed in said injecting position;
    a carrier having a passageway in which the at least one plunger is insertable for advancement of said piston, said carrier shiftable within the interior hollow of said housing from a first axial position to a second axial position, said syringe subassembly engaged by said carrier to be moved axially when said carrier shifts from said first axial position to said second axial position, said syringe subassembly disposed in said injecting position when said carrier is in said first axial position, said needle injection tip disposed in said housing interior hollow between said first and second axial ends when said carrier is in said second axial position;
    at least one latching element shiftably mounted on said carrier, said at least one latching element including a cammable surface and a latch surface, said at least one latching element shiftable relative to the carrier from a retracted arrangement to a latching arrangement by the at least one plunger engaging said cammable surface during advancement of the at least one plunger,
    said latch surface, when said at least one latching element is disposed in said latching arrangement, restricting a size of the passageway to prevent withdrawal of the at least one plunger from the passageway due to interference by said latch surface with the latch abutment surface;
    wherein said carrier, upon retraction of the at least one plunger in a direction opposite said advancing direction while the at least one latching element is in said latching arrangement such that the latch abutment surface engages said latch surface, is lifted within said housing to shift from said first axial position to said second axial position to retract the injection tip into the housing interior hollow, wherein at said second axial position of said carrier said at least one latching element is shiftable from said latching arrangement toward said retracted arrangement to move said latch surface clear of said latch abutment surface to allow withdrawal of the at least one plunger from the passageway without further lifting of said carrier.

2. The refill module of claim 1 wherein said at least one latching element includes a tab that inserts within an opening in said housing to axially located said carrier within said housing prior to use of the refill module.

3. The refill module of claim 1 wherein said at least one latching element includes means engagable with said carrier for biasing said latching element from said latching arrangement to said retracted arrangement.

4. The refill module of claim 1 wherein said at least one latching element slides radially inward within said carrier when shifted from said retracted arrangement to said latching arrangement.

5. The refill module of claim 2 wherein said carrier, when in said second axial position, projects from the housing interior hollow and beyond said housing first axial end, and wherein said tab when in said retracted arrangement radially projects from said carrier to extend over said housing first axial end to thereby prevent plunging of said carrier back into the housing interior hollow by abutting engagement of said tab with said housing first axial end.

6. The refill module of claim 2 further comprising means for rotating said carrier within said housing as said carrier is moved from a storage position to said first axial position, whereby said tab is moved out of angular alignment with said housing opening.

7. The refill module of claim 1 wherein said at least one latching element comprises three latching elements equally angularly spaced around the carrier.

* * * * *